(12) United States Patent
Shirley et al.

(10) Patent No.: US 6,573,238 B2
(45) Date of Patent: *Jun. 3, 2003

(54) METHOD FOR PRODUCING SUSTAINED-RELEASE FORMULATIONS

(75) Inventors: Bret Shirley, Concord, CA (US); Maninder Hora, Danville, CA (US); Derek O'Hagan, Berkeley, CA (US); Manmohan Singh, Hercules, CA (US)

(73) Assignee: Chiron Corporation, Emeryville, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/187,780

(22) Filed: Nov. 6, 1998

(65) Prior Publication Data

US 2002/0013273 A1 Jan. 31, 2002

Related U.S. Application Data

(60) Provisional application No. 60/096,066, filed on Aug. 11, 1998, and provisional application No. 60/064,891, filed on Nov. 7, 1997.

(51) Int. Cl.[7] .......................... A61K 38/00; A61K 9/14; A61K 38/28
(52) U.S. Cl. .............................. 514/12; 514/13; 514/14; 514/15; 424/457; 424/426; 424/468; 424/480; 424/489; 424/490; 424/499; 530/303
(58) Field of Search ................................. 424/426, 457, 424/468, 480, 489, 490, 499; 514/12, 13, 14, 15; 530/303

(56) References Cited

U.S. PATENT DOCUMENTS

| | | | |
|---|---|---|---|
| 3,773,919 A | 11/1973 | Boswell, Jr. et al. | 424/19 |
| 4,542,025 A | 9/1985 | Tice et al. | 424/78 |
| 4,767,628 A | 8/1988 | Hutchinson | 424/426 |
| 5,126,324 A | 6/1992 | Clark et al. | 514/12 |
| 5,134,122 A | 7/1992 | Orsolini | 514/15 |
| 5,374,620 A | 12/1994 | Clark et al. | 514/12 |
| 5,681,814 A | 10/1997 | Clark et al. | 514/12 |
| 6,080,429 A | * 6/2000 | Cleland et al. | 424/489 |

FOREIGN PATENT DOCUMENTS

| | | |
|---|---|---|
| EP | 0 442 671 A2 | 8/1991 |
| WO | WO 94/12158 | 6/1994 |
| WO | WO 95/11009 | 4/1995 |
| WO | WO 96/37216 | 11/1996 |
| WO | WO 99/24062 | 5/1999 |

OTHER PUBLICATIONS

Cleland et al., "Recombinant Human Growth Hormone Poly (Lactic–Co–Glycolic Acid) (PLGA) Microspheres Porvide a Long Lasting Effect," *J. Controlled Release* 49:193–205 (1997).
Hora et al., "Controlled Release of Interleukin–2 From Biodegradable Microspheres," *Bio/Technology* 8:755–758 (1990).
Johnson et al., "A Month–Long Effect from a Single Injection of Microencapsulated Human Growth Hormone," *Nature Medicine* 2(7):795–799 (1996).
Lam et al., "Sustained Release of Recombinant Human Insulin–like Growth Factor–I for Treatment of Diabetes," *American Assn. of Pharmaceutical Scientists*, Western Regional Meeting, Apr. 24–25, 1997, South San Francisco.
Tada et al., "Controlled Release System for IGF–I," *Proceed. Int'l. Symp. Control. Rel. Bioact. Mater.* 24:889–890 (1997).
Jeffrey, Haley, et al., "The Preparation and Characterization of Poly(lactide–co–glycolide) Microparticles. II. The Entrapment of a Model Protein Using a (water–in–Oil)–in–Water Emulsion Solvent Evaporation Technique," *Pharmaceutical Research* 10:362–368 (1993).
Hofrichter et al., "Kinetics and Mechanism of Deoxyhemoglobin S Gelation: A New Approach to Understanding Sickle Cell Disease," *Proc. Nat. Acad. Sci. USA* 71(12):4864–4868 (1974).
Johnson et al., "The Stabilization and Encapsulation of Human Growth Hormone Into Biodegradable Microspheres," *Pharmaceutical Research* 14(6):730–735 (1997).

* cited by examiner

Primary Examiner—Christopher S. F. Low
Assistant Examiner—Chih-Min Kam
(74) Attorney, Agent, or Firm—Roberta L. Robins; Joseph H. Guth; Robert P. Blackburn

(57) ABSTRACT

Methods for preparing biodegradable microparticles are provided. Also provided are microparticles prepared by the method which include IGF-1 entrapped therein. The microparticles allow for controlled release of IGF-1 and other polypeptides over prolonged periods of time.

39 Claims, 6 Drawing Sheets

METHOD FOR PRODUCING SUSTAINED-RELEASE FORMULATIONS

CROSS-REFERENCE TO RELATED APPLICATIONS

This application is related to provisional patent applications serial Nos. 60/096,066, filed Aug. 11, 1998 and 60/064,891, filed Nov. 7, 1997, from which priority is claimed under 35 USC §119(e)(1) and which applications are incorporated herein by reference in their entireties.

TECHNICAL FIELD

The present invention relates generally to pharmaceutical compositions. In particular, the invention relates to methods for preparing biodegradable microparticles, as well as compositions comprising biodegradable microparticles including entrapped polypeptides, such as IGF-1, for sustained-release.

BACKGROUND OF THE INVENTION

Insulin-like growth factor-I (IGF-1) belongs to a family of polypeptides known as somatomedins. IGF-1 is structurally and functionally similar to, but antigenically distinct from, insulin. In this regard, IGF-1 is a single-chain polypeptide with three intrachain disulfide bridges and four domains known as the A, B, C and D domains, respectively. The A and B domains are connected by the C domain, and are homologous to the corresponding domains of proinsulin. The D domain, a carboxy terminal extension, is present in IGF-1 but is absent from proinsulin. IGF-1 has 70 amino acid residues and a molecular mass of approximately 7.5 kDa. Rinderknecht, *J. Biol. Chem.* (1978) 253:2769; and Rinderknecht, *FEBS Lett.* (1978) 89:283. For a review of IGF, see Humbel, *Eur. J. Biochem.* (1990) 190:445–462.

IGF-1 has been reported to stimulate growth and division of a variety of cell types, particularly during development. See, e.g., EP 560,723 A and 436,469 B. IGF-1 has also been shown to be useful for the treatment of osteoporosis. See, for example, U.S. Pat. No. 5,374,620. Thus, processes such as skeletal growth and cell replication are affected by IGF-1 levels. Furthermore, IGF-1 has been reported to be useful in the treatment of pancreatic disorders (WO 93/25226), renal diseases (U.S. Pat. No. 5,106,832) and cardiac disorders (U.S. Pat. No. 5,434,134).

Due to the widely varied clinical applications for IGF-1, compositions with desirable characteristics are in great demand and several IGF-1 formulations have been made. See, e.g., U.S. Pat. Nos. 5,126,324, 5,374,620 and 5,681,814. These compositions are typically formulated as liquid injectables for parenteral delivery. However, such compositions often require frequent injections which are inconvenient, uncomfortable and subject to poor patient compliance. Furthermore, several disorders for which treatment with IGF-1 is indicated require high doses of IGF-1 not achievable by conventional modes of delivery. Thus, there is a need for IGF-1 compositions which allow for controlled, sustained-delivery of adequate doses of IGF-1.

Particulate carriers have been used in order to achieve controlled, parenteral delivery of therapeutic compounds. Such carriers are designed to maintain the active agent in the delivery system for an extended period of time. Examples of particulate carriers include those derived from polymethyl methacrylate polymers, as well as microparticles derived from poly(lactides) (see, e.g., U.S. Pat. No. 3,773,919) and poly(lactide-co-glycolides), known as PLG (see, e.g., U.S. Pat. No. 4,767,628). Polymethyl methacrylate polymers are nondegradable while PLG particles biodegrade by random nonenzymatic hydrolysis of ester bonds to lactic and glycolic acids which are excreted along normal metabolic pathways.

Slow-release formulations containing various polypeptide growth factors have been described. For example, International Publication No. WO 94/12158 describes growth hormone controlled-release systems formed by spraying a polymer and dry protein into a freezing solution of liquid nitrogen to form polymeric microspheres. U.S. Pat. No. 5,134,122 describes methods of forming microparticles that include salts of peptides such as LHRH. International Publication No. WO 96/37216 describes IGF-1 formulations comprising IGF-1 and hydrophobic polymers. Lam et al., *Am. Assn. Pharm. Sci.* Western Regional Meeting (Apr. 24–25, 1997) Abstract F-21 and Tada et al., *Proc. Intl. Symp. Control. Rel. Bioact. Mater.* (1997) 24:889–890, describe IGF-1 PLG microspheres formed by a spray freeze-drying technique and European Publication No. EP 442,671 A2 describes microcapsules containing various polypeptides.

However, the controlled release of adequate amounts of IGF-1 and other proteins over a defined period remains difficult to achieve. Thus, there is a continued need for IGF-1 sustained-release formulations, as well as methods of preparing microparticle compositions that provide for the continuous release of polypeptides.

DISCLOSURE OF THE INVENTION

The present invention is based on the surprising discovery that the use of biodegradable microparticles, such as those derived from a poly($\alpha$-hydroxy acid), and including IGF-1 entrapped in the form of a highly concentrated viscous "syrup", provide for continuous delivery of IGF-1 for extended periods of time. This syrup has an IGF-I concentration of at least about 250 mg/ml, a density of about 1.0 g/ml to about 1.2 g/ml, and a viscosity of about 13,000 centipoise (cps) to about 19,000 cps, as measured at ambient temperature (23° C.)

Additionally, the present invention provides a particularly efficient method for incorporating a desired polypeptide into a biodegradable microparticle by first preparing the polypeptide of interest in a highly concentrated, viscous form and carrying out microparticle formation at lowered, yet not freezing, temperatures. The method allows increased amounts of the protein of interest, e.g., 90% or more of the protein provided, to be incorporated into the microparticle.

Accordingly, in one embodiment, the invention is directed to a method of making a biodegradable microparticle comprising:

(a) preparing a polypeptide in a highly concentrated viscous form;

(b) combining the polypeptide with a polymer selected from the group consisting of a poly($\alpha$-hydroxy acid), a polyhydroxybutyric acid, a polycaprolactone, a polyorthoester and a polyanhydride, wherein the polymer is present at a concentration of about a 1%–30% in an organic solvent and further wherein the polypeptide is present at 0.1% to about 40% (w/w);

(c) emulsifying the polymer/polypeptide solution to form an emulsion;

(d) adding an emulsion stabilizer to the emulsion under conditions that allow microparticles to form;

(e) removing organic solvent from the stabilized emulsion; and (f) recovering the microparticles.

In another embodiment, the invention is directed to a method of making a biodegradable microparticle comprising:

(a) preparing an IGF-1 or IGF-1 analog composition at a pH of about pH 5.5 to about pH 6.0, in a highly concentrated viscous syrup;

(b) cooling the IGF-1 or IGF-1 analog composition to a temperature of about 2° C. to about 8° C.;

(c) combining the cooled IGF-1 or IGF-1 analog composition with a poly(α-hydroxy acid) polymer selected from the group consisting of poly(L-lactide), poly(D, L-lactide) and poly(D,L-lactide-co-glycolide), wherein the polymer is present at a concentration of about 5%–20% in methylchloride and further wherein the IGF-1 is present at about 3% to about 20% (w/w);

(d) emulsifying the polymer/IGF-1 solution at a temperature of about 2° C. to about 8° C.;

(e) adding polyvinyl alcohol as an emulsion stabilizer to the polymer/IGF-1 emulsion under conditions that allow microparticles to form;

(f) removing organic solvent from the stabilized polymer/IGF-1 emulsion; and (g) recovering the microparticles.

In yet other embodiments, the invention is directed to microparticles made using the above methods and sustained-release formulations comprising the microparticles.

In still a further embodiment, the invention is directed to a method of delivering IGF-1 or an IGF-1 analog to a vertebrate subject comprising administering to the vertebrate subject a pharmaceutically effective amount of the sustained-release formulations above.

These and other embodiments of the present invention will readily occur to those of ordinary skill in the art in view of the disclosure herein.

DETAILED DESCRIPTION OF THE INVENTION

Figure 1:
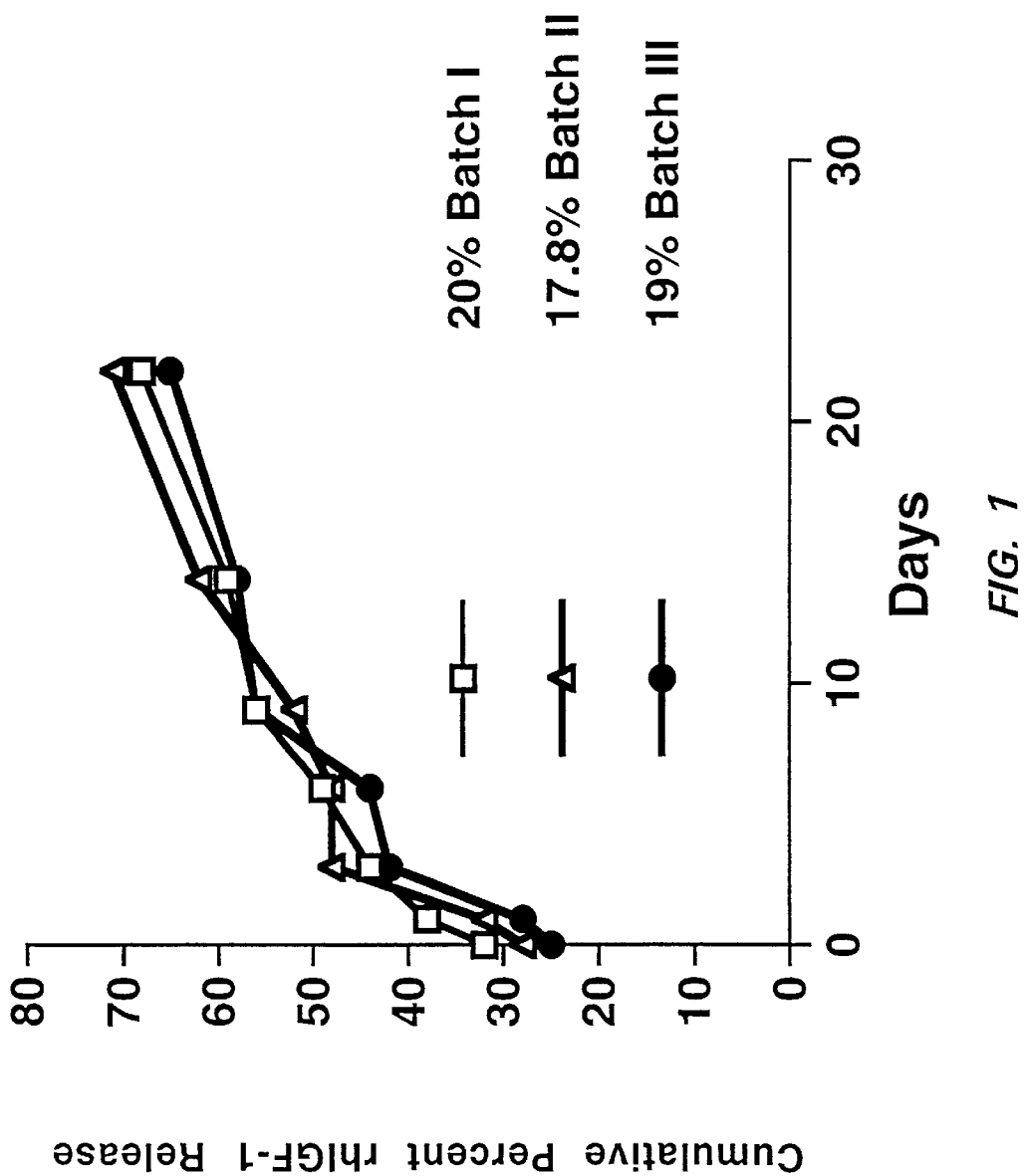
FIG. 1 is a graphical release profile of IGF-1 from PLG microparticles containing an IGF-1 load of 20% (squares), 17.8% (triangles) and 19% (solid circles).

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W. H. Freeman and Company, 1993); A. L. Lehninger, *Biochemistry* (Worth Publishers, Inc., 1975); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa. Mack Publishing Company, 1990).

All publications, patents and patent applications cited herein, whether supra or infra, are hereby incorporated by reference in their entirety.

I. Definitions

In describing the present invention, the following terms will be employed, and are intended to be defined as indicated below.

The term "insulin-like growth factor-1" or "IGF-1" as used herein refers to a compound having the primary, secondary and/or tertiary molecular structure of native IGF-1, and which has at least one IGF-1 activity including activity as measured in standard IGF-1 bioassays and/or the ability to bind IGF receptors. The IGF-1 molecule may include posttranslational modifications, such as glycosylation, acetylation, phosphorylation, etc. Furthermore, the term intends salts and other derivatized forms of IGF-1, which serve to render the IGF-1 less soluble, as described further below.

Additionally, for purposes of the present invention, an IGF-1 may be derived from any of several tissues of any mammalian source, such as human, bovine, canine, equine, ovine, porcine, etc. The IGF-1 compound may be purified directly from the source organism, or may be recombinantly or synthetically produced (see further below).

The term "IGF-1 analog" refers to biologically active derivatives or fragments of IGF-1 that retain IGF-1 activity and/or the ability to bind IGF receptors. Such compounds may include amino acid additions, substitutions (generally conservative in nature) and deletions, relative to the native molecule, so long as the modifications do not destroy IGF-1 activity including activity as measured in standard IGF-1 bioassays and/or the ability of the molecule to bind to IGF receptors. Representative assays include known radioreceptor assays using placental membranes (see, e.g., U.S. Pat. No. 5,324,639; Hall et al., *J. Clin. Endocrinol. and Metab.* (1974) 39:973–976; and Marshall et al., *J. Clin. Endocrinol. and Metab.* (1974) 39:283–292), a bioassay that measures the ability of the molecule to enhance incorporation of tritiated thymidine, in a dose-dependent manner, into the DNA of BALB/c 3T3 fibroblasts (see, e.g., Tamura et al., *J. Biol. Chem.* (1989) 262:5616–5621), and the like. Preferably, the analog has at least the same activity as the native molecule.

IGF-1 analogs will generally have at least 60%, preferably 70%, more preferably 80%, preferably 90% to 95% or more, and most preferably 98% or more, amino acid sequence identity to the amino acid sequence of the reference IGF-1 molecule. In general, "identity" refers to an exact amino acid to amino acid correspondence of two or more polypeptide sequences. For example, the IGF-1 analog may have from about 1 to about 20 amino acid substitutions, e.g., 10, 9, 8, 7, 6, 5, 4, 3, 2 or 1 amino acid substitutions.

Techniques for determining amino acid sequence identity are well known in the art and include comparing the known sequence of IGF-1 to a second amino acid sequence, by e.g., aligning the sequences. Programs available for determining identity between sequences include ALIGN, Dayhoff, M. O. (1978) in *Atlas of Protein Sequence and Structure* 5:Suppl. 3, National biomedical Research Foundation, Washington, DC. and programs in the Wisconsin Sequence Analysis Package, Version 8 (available from Genetics Computer Group, Madison, Wis.) for example, the GAP program. One of skill in the art can readily use such programs, along with the default parameters provided by the manufacturer, in order to assess the percent identity between two polypeptides. Other programs for calculating identity or similarity between sequences are known in the art.

The art provides substantial guidance regarding the preparation and use of such analogs, as discussed further below. A fragment of IGF-1 will generally include at least about 10 contiguous amino acid residues of the full-length molecule, preferably about 15–25 contiguous amino acid residues of the full-length molecule, and most preferably about 20–50 or more contiguous amino acid residues of full-length IGF-1. The term "IGF-1 analog" also captures peptides having one or more peptide mimics ("peptoids"), such as those described in International Publication No. WO 91/04282.

Several IGF-1 analogs and fragments are known in the art and include those described in e.g., *Proc. Natl. Acad. Sci. USA* (1986) 83:4904–4907; *Biochem. Biophys. Res. Commun.* (1987) 149:398–404; *J. Biol. Chem.* (1988) 263:6233–6239; *Biochem. Biophys. Res. Commun.* (1989) 165:766–771; Forsberg et al., *Biochem. J.* (1990) 271:357–363; U.S. Pat. Nos. 4,876,242 and 5,077,276; International Publication No. WO 87/01038 and WO 89/05822. Representative analogs include one with a deletion of Glu-3 of the mature molecule, analogs with up to five amino acids truncated from the N-terminus, an analog with a truncation of the first three N-terminal amino acids and an analog including the first 17 amino acids of the B chain of human insulin in place of the first 16 amino acids of human IGF-1.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like.

For purposes of the present invention, the polypeptide entrapped in the microparticle may be one useful in a vaccine or diagnostic and may be derived from any of several known viruses, bacteria, parasites and fungi, as well as any of the various tumor antigens. Alternatively, the polypeptide may be a therapeutic hormone, a transcription or translation mediator, an enzyme, an intermediate in a metabolic pathway, an immunomodulator, and the like.

Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

By "substantially insoluble" is meant that the polypeptide of interest is provided as a composition in which at least about 60% of the polypeptide of interest is not dissolved, more preferably at least about 75%, even more preferably at least about 85% and most preferably, at least about 90% or more of the polypeptide present is not is dissolved. For purposes of the present invention, substantially insoluble polypeptides are typically provided in the form of a highly concentrated viscous syrup.

By "highly concentrated viscous syrup" or "highly concentrated viscous form" is meant an IGF-1 concentration of at least about 250 mg/ml, for example, at least about 300 mg/ml, or at least about 350 mg/ml, or at least about 425 mg/ml, or about 450 mg/ml to 500 mg/ml, as measured at ambient temperature (23° C.). At these concentrations and temperature, this syrup has a density of about 1.0 g/ml to about 1.2 g/ml, more preferably about 1.1 g/ml, and a viscosity of about 13,000 centipoise (cps) to about 19,000 cps, preferably about 14,000 cps to about 18,000 cps, more preferably about 15,000 cps to about 17,000 cps, still more preferably about 15,500 cps to about 16,500 cps, even more preferably about 16,000 cps. In one embodiment, the syrup has an IGF-1 concentration of about 350 mg/ml, a density of about 1.07 g/ml, and a viscosity of about 15,700 cps, as measured at ambient temperature. Density and viscosity are determined using standard techniques well known in the art. See, commonly owned, copending U.S. patent application Ser. No. 60/096,081, entitled "Novel IGF-1 Composition and Its Use," filed Aug. 11, 1998 and incorporated herein by reference in its entirety. By "low salt-containing" is intended an amount of salt that is insufficient to cause precipitation of the protein. "Biologically active" is intended to mean that the IGF-I or variant, when reconstituted from its syrup form into a solution form, is biologically active without the need for refolding.

This highly concentrated IGF-I syrup is obtained by precipitating IGF-I or variant thereof in accordance with the methods of the present invention. This syrup form of IGF-I is flowable and clear to opalescent in appearance, features that distinguish it from salt-precipitated forms of IGF-I, such as IGF-I prepared by precipitation or "salting out" using, for example, ammonium sulfate. As a result of the high solubility of ammonium sulfate (3.9 M in water at 0° C.), high ionic strength solutions favoring IGF-I precipitation can readily be achieved. See, for example, Voet and Voet (1995) *Biochemistry* (John Wiley and Sons, New York), pp. 79–81. This method results in precipitation of a salt-protein complex that is white in appearance, has the consistency of a thick paste, and has a substantially higher viscosity than the IGF-I syrup of the present invention. Such a precipitated salt-protein complex is not amenable to quick and easy recovery of low salt-containing IGF-I. To retrieve low salt-containing IGF-I, the precipitate would have to be resolubilized (and thereby made less concentrated), followed by removal of salt from the protein solution.

The term "microparticle" as used herein, refers to a particle of about 100 nm to about 150 μm in diameter, more preferably about 200 nm to about 30 μm in diameter, and most preferably about 500 nm to about 10 μm in diameter. Preferably, the microparticle will be of a diameter that permits parenteral administration without occluding needles and capillaries. Microparticle size is readily determined by techniques well known in the art, such as photon correlation spectroscopy, laser diffractometry and/or scanning electron microscopy. Microparticles for use herein will be formed from materials that are sterilizable, non-toxic and biodegradable. Such materials include, without limitation, poly (α-hydroxy acid), polyhydroxybutyric acid, polycaprolactone, polyorthoester, polyanhydride, polyvinyl alcohol and ethylenevinyl acetate. Preferably, microparticles for use with the present invention are derived from a poly(α-hydroxy acid), in particular, from a poly(lactide) ("PLA") or a copolymer of D,L-lactide and glycolide or glycolic acid, such as a poly(D,L-lactide-co-glycolide) ("PLG" or "PLGA"), or a copolymer of D,L-lactide and caprolactone. The microparticles may be derived from any of various polymeric starting materials which have a variety of molecular weights and, in the case of the copolymers such as PLG, a variety of lactide:glycolide ratios, the selection of which will be largely a matter of choice, depending in part on the desired dose of polypeptide and the disorder to be treated. These parameters are discussed more fully below.

As used herein, the term "sustained-release" refers to the release of a polypeptide such as IGF-1 from microparticles over a defined period of time in a continuous, discontinuous, linear or nonlinear manner. For example, release may be essentially biphasic, i.e., the release will include an initial burst of polypeptide from the microparticle, followed by continuous release of the polypeptide from the microparticle over time. Methods of measuring release of a protein from a microparticle over time are well known in the art. See, e.g., Hora et al., *Pharm. Res.* (1990) 7:1190–1194; Hora et al., *Bio/Technology* (1990) 8:755–758; and the examples herein.

The terms "effective amount" or "pharmaceutically effective amount" of polypeptide, as provided herein, refer to a nontoxic but sufficient amount of the polypeptide to provide the desired biological result. That result can be reduction and/or alleviation of the signs, symptoms, or causes of a disease, or any other desired alteration of a biological system. Such amounts are described below. An appropriate "effective" amount in any individual case may be determined by one of ordinary skill in the art using routine experimentation.

As used herein, "treatment" refers to both the prevention of the disease in question and the reduction or elimination of symptoms. Treatment may be effected prophylactically (prior to disease symptoms) or therapeutically (following disease symptoms).

By "pharmaceutically acceptable" or "pharmacologically acceptable" is meant a material which is not biologically or otherwise undesirable, i.e., the material may be administered to an individual along with the microparticle formulations without causing any undesirable biological effects or interacting in a deleterious manner with any of the components of the composition in which it is contained.

By "physiological pH" or a "pH in the physiological range" is meant a pH in the range of approximately 7.2 to 8.0 inclusive, more typically in the range of approximately 7.2 to 7.6 inclusive.

By "vertebrate subject" is meant any member of the subphylum cordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

II. Modes of Carrying Out the Invention

The present invention is based on an efficient and reproducible method of incorporating adequate amounts of a polypeptide of interest into a biodegradable microparticle such that a wide array of disorders may be treated. Particularly, the methods of the present invention provide for the entrapment of polypeptides, provided in a highly concentrated viscous form, within microparticles by forming the microparticles at lowered, but not freezing, temperatures. The method allows for a high percentage of the provided polypeptide, i.e., as high as 90% or more, to become incorporated in the biodegradable microparticle.

The present invention also provides IGF-1 microparticles which allow for the controlled release of polypeptides, such as biologically active IGF-1, for prolonged periods of time. Generally, release is biphasic, with an initial burst of polypeptide from the microparticle, followed by continuous release of the polypeptide over time.

Although the methods of the present invention have been illustrated using IGF-1, almost any protein of therapeutic value may be encapsulated in microparticles using the techniques described herein. For example, the methods of the present invention will find use for encapsulation of a wide variety of substances, including peptides which act as antibiotics and antiviral agents, e.g., immunogenic peptides for use in vaccines and diagnostics; antineoplastics; immunomodulators, such as any of the various cytokines including interleukin-1, interleukin-2, interleukin-3, interleukin-4, interleukin-12, beta-interferon and gamma-interferon; peptide hormones such as insulin, proinsulin, growth hormone, GHRH, LHRH, EGF, somatostatin, SNX-111, BNP, insulinotropin, ANP, FSH, LH, PSH and hCG, gonadal steroid hormones (androgens, estrogens and progesterone), thyroid-stimulating hormone, inhibin, cholecystokinin, ACTH, CRF, dynorphins, endorphins, endothelin, fibronectin fragments, galanin, gastrin, insulinotropin, glucagon, GTP-binding protein fragments, guanylin, the leukokinins, magainin, mastoparans, dermaseptin, systemin, neuromedins, neurotensin, pancreastatin, pancreatic polypeptide, substance P, secretin, thymosin, and the like; and growth factors, such as PDGF, EGF, KGF, IGF-2, FGF, and the like.

More particularly, proteins for use in vaccines and diagnostics may be of viral, bacterial, fungal or parasitic origin, including but not limited to, those encoded by human and animal viruses and can correspond to either structural or non-structural proteins. For example, the present methods will find use with a wide variety of proteins from the herpesvirus family, including proteins derived from herpes simplex virus (HSV) types 1 and 2, such as HSV-1 and HSV-2 glycoproteins gB, gD and gH; proteins derived from varicella zoster virus (VZV), Epstein-Barr virus (EBV) and cytomegalovirus (CMV) including CMV gB and gH; and proteins derived from other human herpesviruses such as HHV6 and HHV7. (See, e.g. Chee et al., *Cytomegaloviruses* (J. K. McDougall, ed., Springer-Verlag 1990) pp. 125–169, for a review of the protein coding content of cytomegalovirus; McGeoch et al., *J. Gen. Virol.* (1988) 69:1531–1574, for a discussion of the various HSV-1 encoded proteins; U.S. Pat. No. 5,171,568 for a discussion of HSV-1 and HSV-2 gB and gD proteins and the genes encoding therefor; Baer et al., *Nature* (1984) 310:207–211, for the identification of protein coding sequences in an EBV genome; and Davison and Scott, *J. Gen. Virol.* (1986) 67:1759–1816, for a review of VZV.)

Proteins from the hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV), can also be conveniently used in the techniques described herein. By way of example, the viral genomic sequence of HCV is known, as are methods for obtaining the sequence. See, e.g., International Publication Nos. WO 89/04669; WO 90/11089; and WO 90/14436. The HCV genome encodes several viral proteins, including E1 (also known as E) and E2 (also known as E2/NS1). (See, Houghton et al., *Hepatology* (1991) 14:381–388, for a discussion of HCV proteins, including E1 and E2.) These proteins, as well as antigenic fragments thereof, will find use in the present methods.

Similarly, the sequence for the δ-antigen from HDV is known (see, e.g., U.S. Pat. No. 5,378,814) and this protein can also be conveniently used in the present methods. Additionally, antigens derived from HBV, such as the core antigen, the surface antigen, sAg, as well as the presurface sequences, preS1 and preS2 (formerly called preS), as well as combinations of the above, such as sAg/preS1, sAg/preS2, sAg/preS1/preS2, and preS1/preS2, will find use herein. See, e.g., "HBV Vaccines—from the laboratory to license: a case study" in Mackett, M. and Williamson, J. D., *Human Vaccines and Vaccination*, pp. 159–176, for a discussion of HBV structure; and U.S. Pat. Nos. 4,722,840, 5,098,704, 5,324,513, incorporated herein by reference in their entireties; Beames et al., *J. Virol.* (1995) 69:6833–6838, Birnbaum et al., *J. Virol.* (1990) 64:3319–3330; and Zhou et al., *J. Virol.* (1991) 65:5457–5464.

Proteins derived from other viruses will also find use in the claimed methods, such as without limitation, proteins from members of the families Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae (e.g., HTLV-I; HTLV-II; HIV-1 (also known as HTLV-III, LAV, ARV, hTLR, etc.)), including but not limited to antigens from the isolates $HIV_{IIIb}$, $HIV_{SF2}$, $HIV_{LAV}$, $HIV_{LAI}$, $HIV_{MN}$); HIV-$1_{CM235}$, HIV-$1_{US4}$; HIV-2; simian immunodeficiency virus (SIV) among others. See, e.g. Virology, 3rd Edition (W. K. Joklik ed. 1988); *Fundamental Virology*, 2nd Edition (B. N. Fields and D. M. Knipe, eds. 1991), for a description of these and other viruses.

For example, the invention may be used to entrap the gp120 envelope protein from any of the above HIV isolates. The gp120 sequences for a multitude of HIV-1 and HIV-2 isolates, including members of the various genetic subtypes of HIV, are known and reported (see, e.g., Myers et al., Los Alamos Database, Los Alamos National Laboratory, Los Alamos, N.Mex. (1992); Myers et al., *Human Retroviruses and Aids,* 1990, Los Alamos, N.Mex.: Los Alamos National Laboratory; and Modrow et al., *J. Virol.* (1987) 61:570–578, for a comparison of the envelope sequences of a variety of HIV isolates) and sequences derived from any of these isolates will find use in the present methods. Furthermore, the invention is equally applicable to other immunogenic proteins derived from any of the various HIV isolates, including any of the various envelope proteins such as gp160 and gp41, gag antigens such as p24gag and p55gag, as well as proteins derived from the pol region.

The present invention will also find use with influenza virus proteins. Specifically, the envelope glycoproteins HA and NA of influenza A are of particular interest for generating an immune response. Numerous HA subtypes of influenza A have been identified (Kawaoka et al., *Virology* (1990) 179:759–767; Webster et al., "Antigenic variation among type A influenza viruses," p. 127–168. In: P. Palese and D. W. Kingsbury (ed.), *Genetics of influenza viruses.* Springer-Verlag, New York). Thus, proteins derived from any of these isolates can also be used in the techniques described herein.

Furthermore, the methods described herein provide a means for entrapping proteins useful for treating a variety of malignant cancers, such as a wide variety of tumor antigens which in turn may be used to mount both humoral and cell-mediated immune responses to particular proteins specific to the cancer in question, such as an activated oncogene, a fetal antigen, or an activation marker. Such tumor antigens include any of the various MAGEs (melanoma associated antigen E), including MAGE 1, 2, 3, 4, etc. (Boon, T. *Scientific American* (March 1993):82–89); any of the various tyrosinases; MART 1 (melanoma antigen recognized by T cells), mutant ras; mutant p53; p97 melanoma antigen; CEA (carcinoembryonic antigen), among others.

It is readily apparent that the subject methods can be used to entrap a variety of proteins useful for the prevention, treatment and/or diagnosis of a wide variety of diseases.

Polypeptides for use in the subject methods, can be produced in any number of ways which are well known in the art. For example, the polypeptides can be isolated directly from a tissue or organ that produces the same. In the case of IGF-1, the polypeptide can be isolated from blood, such as from serum or plasma, by known methods. See, e.g., U.S. Pat. No. 4,769,361; Svoboda et al., *Biochemistry* (1980) 19:790–797; Cornell and Boughdady, *Prep. Biochem.* (1982) 12:57; and Cornell and Boughdady, *Prep. Biochem.* (1984) 14:123. Alternatively, polypeptides for use in the subject methods can be synthesized chemically, by any of several techniques that are known to those skilled in the peptide art. See, e.g., J. M. Stewart and J. D. Young, *Solid Phase Peptide Synthesis* (Pierce Chemical Co., Rockford, Ill. 1984) and G. Barany and R. B. Merrifield, *The Peptides: Analysis, Synthesis, Biology*, editors E. Gross and J. Meienhofer, Vol. 2, (Academic Press, New York, 1980), pp. 3–254, for solid phase peptide synthesis techniques; and M. Bodansky, *Principles of Peptide Synthesis*, (Springer-Verlag, Berlin 1984) and E. Gross and J. Meienhofer, Eds., *The Peptides: Analysis, Synthesis, Biology*, Vol. 1, for classical solution synthesis. The polypeptides of the present invention can also be chemically prepared by the method of simultaneous multiple peptide synthesis. See, e.g., Houghten *Proc. Natl. Acad. Sci. USA* (1985) 82:5131–5135; U.S. Pat. No. 4,631,211.

Preferably, the polypeptides are obtained using recombinant methods well known in the art. See, e.g., Sambrook et al., supra. For example, the recombinant production of IGF-1 in bacterial and yeast hosts and purification therefrom has been described. See, e.g., International Publication Nos. WO 96/40776, WO 96/07744, WO 95,06059, WO 95/06064, WO 95/16777, WO 93/11240 and WO 92/04363; EP 567,554 B; U.S. Pat. Nos. 5,650,496, 5,612,198, 5,407, 810, 5,410,026, 5,288,931, 5,324,639 and 5,231,178; Chang and Swartz, *Protein Folding: in vivo and in vitro* (American Chemical Society, 1993) pp. 178–188; Elliott et al., *J. Protein Chem.* (1990) 9:95–104.

In particular, IGF-1 can be produced in methylotrophic yeast transformants, such as in a protease deficient *P. pastoris* strain as well as in *Saccharomyces cerevisiae* (see, e.g., U.S. Pat. Nos. 5,231,178, 5,324,639, 5,612,198 and 5,650, 496; International Publication Nos. WO 96/40776, WO 96/07744, WO 92/04363; and EP 567,554 B, all of which are incorporated herein by reference in their entireties).

The IGF-1 will either be secreted, if appropriate leader sequences are used, or produced intracellularly and the cells manipulated to allow proper isolation of an IGF-containing product. Particularly preferred methods for producing IGF-1, e.g. in yeast, generally utilize a secretion leader, such as a leader sequence derived from the yeast α-factor signal sequence, as described in EP 128 733. Production in yeast generally includes a fermentation step for cell amplification, followed by purification and refolding to obtain an authentic, properly folded protein. Methods for fermenting the culture, purification and refolding are well known in the art. See, e.g., U.S. Pat. Nos. 5,324,639 and 5,650,496, and International Publication Nos. WO 96/07744 and WO 96/40776, incorporated herein by reference in their entireties.

Once obtained, the polypeptide is prepared in a highly concentrated, viscous form for subsequent entrapment within microparticles in accordance with the method of the present invention. Entrapment of the polypeptide in this viscous state allows for controlled release of the polypeptide from the microparticles over prolonged periods of time. The viscous form of the polypeptide may be prepared using any method that reduces solubility of the polypeptide. Protein solubility may be reduced using any number of techniques well known in the art. Preferably, the method used will not affect biological activity of the polypeptide when released from the microparticles.

In the case of IGF-1, a highly concentrated viscous form of this protein may be prepared by reducing solubility using the methods disclosed in detail in commonly owned, copending U.S. patent application Ser. No. 60/096,081, entitled "Novel IGF-1 *Composition and Its Use*," filed Aug. 11, 1998 and incorporated herein by reference in its entirety. This highly concentrated form of IGF-1 has a concentration of at least about 250 mg/ml and has the consistency of a viscous syrup. The IGF-1 syrup has a low concentration of salt, and the IGF-1 is biologically active without the need for refolding. Thus, when the entrapped IGF-1 is released from the microparticles into a physiological setting, it retains biological activity similar to that of IGF-1 that has not been rendered in this viscous form.

The first of these methods comprises reducing the solubility of IGF-1 such that IGF-1 is precipitated from a buffer solution containing the IGF-1. Precipitation is achieved by adjusting the pH of the IGF-1-containing buffer solution to a pH above about pH 5.0. Accordingly, IGF-1 is prepared in a buffer solution having an initial pH of less than about pH 5.0, preferably about pH 2.0 to about pH 5.0, more preferably about pH 3.0 to about pH 4.5, even more preferably about pH 3.5 to about pH 4.0. The initial concentration of IGF-1 in this low pH buffer solution will determine the amount of the highly concentrated IGF-1 syrup obtained following upward adjustment of pH. Thus, a higher initial concentration of IGF-1 will yield a greater amount of precipitated IGF-1 syrup. Regardless of the initial concentration of IGF-1, the concentration of the precipitated IGF-1 is at least about 250 mg/ml as noted above.

In order to obtain this highly concentrated IGF-1 syrup, the initial pH of the buffer solution containing IGF-1 is adjusted upward to a final pH greater than about pH 5.0, preferably to a pH of greater than about 5.0 to about 9.0, more preferably to a pH of greater than about 5.0 to about 8.0, still more preferably to a pH of about 5.5 to about 7.0, even more preferably to a pH of about 5.5 to about 6.5, and most preferably to a pH of about 5.5 to about 6.0. As pH is increased, IGF-1 above the solubility limit at the higher pH conditions precipitates, forming a viscous syrup.

The pH of the buffer solution may be adjusted by standard titrating procedures will known in the art, such as with addition of sodium hydroxide. Alternatively, solution pH may be adjusted by dialyzing the initial buffer solution containing IGF-1 against any suitable buffer solution having the desired final pH above pH 5.0 as disclosed above. Such buffers include, for example, inorganic (e.g., phosphate) and organic (e.g., acetate) buffers. In one embodiment of the invention, the IGF-1 buffer solution having an initial pH less than or equal to pH 5.0 is dialyzed against a sodium citrate buffer at pH 6.0.

This highly concentrated IGF-1 syrup can also be prepared using an appropriate solubilizing agent or so-called solubility enhancer. By "solubility enhancer" is intended a compound that includes a guanidinium group and that is capable of enhancing the solubility of IGF-1 or a variant of IGF-1. Examples of such solubilizing compounds include the amino acid arginine, as well as amino acid analogs of arginine that retain the ability to enhance solubility of IGF-1 at pH 5.5 or greater. Such analogs include, without limitation, dipeptides and tripeptides that contain arginine. By "enhancing the solubility" of IGF-1 is meant increasing the amount of IGF-1 that can be dissolved in solution at pH 5.5 or greater, 6.0 or greater, 7.0 or greater, 8.0 or greater, or 9.0 or greater in the presence of a guanidinium-containing compound compared to the amount of IGF-1 that can be dissolved at pH 5.5 or greater, 6.0 or greater, 7.0 or greater, 8.0 or greater, or 9.0 or greater, respectively, in a solution with the same components but lacking in the guanidinium-containing compound. The ability of a guanidinium-containing compound to enhance the solubility of a IGF-1 can be determined using methods well known in the art. In general, the concentration of the solubilizing compound present in the composition is from about 10 mM to about 1 M, and, for example, in the case of the compound arginine, in a concentration range of about 20 mM to about 200 mM, as disclosed in the commonly owned, copending U.S. application Ser. No. 60/064,891, filed Nov. 7, 1997.

In this manner, addition of a solubility enhancer to the solution allows for the preparation of a highly concentrated IGF-1 solution. The solubility enhancer is then removed from this IGF-1 solution by dialysis or diafiltration. Removal of the solubility enhancer results in precipitation of IGF-1 in the highly concentrated syrup form. The soluble portion of IGF-1 can then be decanted off, and the IGF-1 syrup recovered.

An alternative method for reducing solubility of polypeptide such as IGF-1 involves complexing the protein with a divalent metal, such as Cu++, Mn++, Ni++, Zn++ and/or Fe++. Methods for complexing proteins with such metals are known in the art. See, e.g., Johnson et al., *Nature Med.* (1996) 2:795.

Additionally, solubility of polypeptides may be reduced by forming acid addition salts (formed with the free amino groups of the polypeptide) with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like. Furthermore, the polypeptides can be provided in the form of a pamoate, tannate, stearate or palmitate salt. See, e.g., U.S. Pat. No. 5,134,122.

Protein solubility can also be reduced using biological cations (see, e.g., International Publication No. WO 92/11844) or complexing agents such as albumin or protamine, at ratios of about 1:10 to about 4:1, complexing agent to IGF-1.

It is important to note that the present invention distinguishes from prior techniques because the polypeptide itself is rendered insoluble, rather than by addition of gelling agents to the polypeptide/polymer solution.

Additionally, the polypeptides can be formulated with protein stabilizers in order to preserve the activity thereof. Such stabilizers are known in the art and include, e.g., simple salts, buffer salts, polyhdroxylated compounds such as glycerol, mannitol, sucrose and polyethylene glycols, and surfactants. See, e.g., International Publication No. WO 92/11844.

After the polypeptide is prepared in a highly concentrated, viscous form, it is combined with appropriate polymers to form microparticles for subsequent delivery, as described further below. Prior to doing so, the polypeptide may be cooled to a temperature of approximately 1° C. to about 20° C., more preferably about 2° C. to about 10° C., even more preferably about 2° C. to about 8° C., and most preferably to about 4° C.

Biodegradable polymers for manufacturing microparticles useful in the present invention are readily commercially available from, e.g., Boehringer Ingelheim, Germany and Birmingham Polymers, Inc., Birmingham, Ala. For example, useful polymers for forming the microparticles herein include those derived from: polyhydroxybutyric acid; polycaprolactone; polyorthoester; polyanhydride; polyvinyl alcohol; ethylenevinyl acetate; as well as a poly($\alpha$-hydroxy acid), such as poly(L-lactide), poly(D,L-lactide) (both known as "PLA" herein), poly(hydoxybutyrate), copolymers of D,L-lactide and glycolide, such as poly(D,L-lactide-co-glycolide) (designated as "PLG" or "PLGA" herein) or a copolymer of D,L-lactide and caprolactone.

Particularly preferred polymers for use herein are PLA and PLG polymers. These polymers are available in a variety of molecular weights, and the appropriate molecular weight to provide the desired release rate for the polypeptide in question is readily determined by one of skill in the art. Thus, e.g., for PLA, a suitable molecular weight will be on the order of about 2000 to 250,000. For PLG, suitable molecular weights will generally range from about 10,000 to about 200,000, preferably about 15,000 to about 150,000, and most preferably about 50,000 to about 100,000.

If a copolymer such as PLG is used to form the microparticles, a variety of lactide:glycolide ratios will find use herein and the ratio is largely a matter of choice, depending in part on the rate of degradation desired. For example, a 50:50 PLG polymer, containing 50% D,L-lactide and 50% glycolide, will provide a fast resorbing copolymer while 75:25 PLG degrades more slowly, and 85:15 and 90:10, even more slowly, due to the increased lactide component. It is readily apparent that a suitable ratio of lactide-:glycolide is easily determined by one of skill in the art based on the nature disorder to be treated. Moreover, mixtures of microparticles with varying lactide:glycolide ratios will find use in the formulations in order to achieve the desired release kinetics. PLG copolymers with varying lactide:glycolide ratios and molecular weights are readily available commercially from a number of sources including from Boehringer Ingelheim, Germany and Birmingham Polymers, Inc., Birmingham, Ala. These polymers can also be synthesized by simple polycondensation of the lactic acid component using techniques well known in the art, such as described in Tabata et al., *J. Biomed. Mater. Res.* (1988) 22:837–858.

The microparticles are prepared using any of several methods well known in the art, the critical parameter being that the highly concentrated, viscous form of the protein is added to the polymer solution at a low temperature, as explained above. For example, double emulsion/solvent evaporation techniques, such as described in U.S. Pat. No. 3,523,907 and Ogawa et al., *Chem. Pharm. Bull.* (1988) 36:1095–1103, can be used herein to form the microparticles. These techniques involve the formation of a primary emulsion consisting of droplets of polymer solution containing the IGF-1, which is subsequently mixed with a continuous aqueous phase containing a particle stabilizer/surfactant.

More particularly, a water-in-oil-in-water (w/o/w) solvent evaporation system can be used to form the microparticles, as described by O'Hagan et al., *Vaccine* (1993) 11:965–969 and Jeffery et al., *Pharm. Res.* (1993) 10:362. In this technique, the particular polymer is combined with an organic solvent, such as ethyl acetate, methylene chloride (also called dimethylene chloride and dichloromethane), acetonitrile, acetone, chloroform, and the like. The polymer will be provided in about a 1%–30% (w/v) solution, more preferably about a 3%–25% solution and most preferably, about a 5%–20% solution, in organic solvent. An amount of the desired polypeptide preparation will be added to the polymer solution to provide a ratio of polymer:polypeptide from about 60:40 to about 99.9:0.1, preferably about 75:25, and most preferably about 97:3. The polymer/polypeptide solution is emulsified using e.g., an homogenizer. The emulsion is then combined with a larger volume of an aqueous solution of an emulsion stabilizer such as polyvinyl alcohol (PVA) or polyvinyl pyrrolidone. The emulsion stabilizer is typically provided in about a 2–15% solution, more typically about a 4–10% solution. The mixture is then homogenized to produce a stable w/o/w double emulsion. organic solvents are then evaporated.

The formulation parameters can be manipulated to allow the preparation of small (<5 $\mu$m) and large (>30 $\mu$m) microparticles. See, e.g., Jeffery et al., *Pharm. Res.* (1993) 10:362–368; McGee et al., *J. Microencap.* (1996). For example, reduced agitation results in larger microparticles, as does an increase in internal phase volume. Small particles are produced by low aqueous phase volumes with high concentrations of PVA.

Microparticles can also be formed using spray-drying and coacervation as described in, e.g., Thomasin et al., *J. Controlled Release* (1996) 41:131; U.S. Pat. No. 2,800,457; Masters, K. (1976) *Spray Drying* 2nd Ed. Wiley, New York; air-suspension coating techniques, such as pan coating and Wurster coating, as described by Hall et al., (1980) The "Wurster Process" in *Controlled Release Technologies: Methods, Theory, and Applications* (A. F. Kydonieus, ed.), Vol. 2, pp. 133–154 CRC Press, Boca Raton, Fla. and Deasy, P. B., *Crit. Rev. Ther. Drug Carrier Syst.* (1988) S(2) :99–139; and ionic gelation as described by, e.g., Lim et al., *Science* (1980) 210:908–910.

In the above methods, emulsification is carried out at lowered temperatures, but not freezing, in order to maintain a viscous, gel-like emulsion. Generally, the emulsification procedure will be carried out at a temperature of approximately 1° C. to about 20° C., more preferably about 2° C. to about 10° C., even more preferably about 2° C. to about 8° C., and most preferably to about 4° C. The proper conditions for achieving the desired viscosity can be readily determined by one of skill in the art.

Degradation of the particles is by hydrolysis of ester linkages in the backbone. Therefore, the rate of degradation may be controlled by changing polymer properties that influence water uptake, such as by adjusting the hydrophilicy and crystallinity of the particle which, in turn, determines the rate of water penetration. As explained above, one way of controlling the degradation rate is by adjusting the monomer ratio (e.g., lactide:glycolide). Degradation rate may also be controlled by such factors as the particular monomer used (e.g., L-lactide versus D,L-lactide), polymer molecular weight, as well as the presence of polymer degradation modifiers and pore forming agents, all well known in the art. See, e.g., International Publication No. WO 94/12158. Degradation rate may also be controlled by the amount of polypeptide present in the microparticles (see further below for appropriate amounts).

Thus, for example, a microparticle formed of poly(L-lactide), or a high molecular weight poly(lactide-co-glycolide) polymer with low glycolide amounts, will exhibit slow erosion and cause release of the polypeptide to be governed largely by diffusion. On the other hand, water uptake and hydrolysis of the polymer can be enhanced by increasing the glycolide concentration and lowering the molecular weight. Additionally, hydrophilic excipients such as salts, carbohydrates and surfactants can also be incorporated to increase water penetration into the microparticles thereby accelerating erosion of the polymer. Pore forming agents include substances that add microstructure to the particles, for example, water soluble compounds such as inorganic salts and sugars, present in the range of about 1% to about 30% (w/w polymer). One of skill in the art can readily vary the above parameters in order to produce a microparticle with desired degradation characteristics.

In general, a microparticle which delivers a polypeptide over a period of at least about 24 hours up to 2–3 months or more, more preferably over a period of at least about 1 week, and even more preferably over a period of about 2–4 weeks or more, is desirable. Methods of measuring release of a protein from a microparticle over time are well known in the art. See, e.g., Hora et al., *Pharm. Res.* (1990) 7:1190–1194; Hora et al., *Bio/Technology* (1990) 8:755–758; and the examples herein.

Particle size can be determined by, e.g., laser light scattering, using for example, a spectrometer incorporating a helium-neon laser. Generally, particle size is determined at room temperature and involves multiple analyses of the sample in question (e.g., 5–10 times) to yield an average value for the particle diameter. Particle size is also readily determined using scanning electron microscopy (SEM).

Prior to use of the microparticles, protein content is generally determined so that an appropriate amount of the microparticles may be delivered to the subject in order to elicit an appropriate biological response. Protein content of the microparticles can be determined according to methods known in the art, such as by disrupting the microparticles and extracting the entrapped polypeptide. For example, microparticles can be dissolved in methylene chloride and the protein extracted into distilled water, as described in, e.g., Cohen et al., *Pharm. Res.* (1991) 8:713; Eldridge et al., *Infect. Immun.* (1991) 59:2978; and Eldridge et al., *J. Controlled Release* (1990)11:205. Alternatively, microparticles can be dispersed in 0.1 M NaOH containing 5% (w/v) SDS. The sample is agitated, centrifuged and the supernatant assayed for the particular polypeptide using an appropriate assay. See, e.g., O'Hagan et al., *Int. J. Pharm.* (1994) 103:37–45.

For purposes of the present invention, preferably the particles comprise from about 0.1% to about 40% (w/w) polypeptide, more preferably about 2% to about 25% (w/w) polypeptide, and even more preferably about 3%–4% to about 18%–20% (w/w) polypeptide. The load of polypeptide in the microparticles will depend on the desired dose and the condition being treated, as discussed in more detail below.

Once formulated, the microparticles of the present invention are generally combined with a pharmaceutically acceptable excipient or vehicle, including liquids such as water, saline, glycerol, polyethyleneglycol, hyaluronic acid, ethanol, etc. Suitable excipients for nonliquid formulations are also known to those of skill in the art. Pharmaceutically acceptable salts can be used in the compositions of the present invention and include, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients and salts is available in *Remington's Pharmaceutical Sciences*, 18th Edition (Easton, Pa. Mack Publishing Company, 1990).

Additionally, auxiliary substances, such as wetting or emulsifying agents, biological buffering substances, surfactants, and the like, may be present in such vehicles. A biological buffer can be virtually any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Once formulated, the compositions of the invention are generally administered parenterally. Administration can include, for example, administration intravenously, intra-arterially, intra-articularly (e.g., into the knee), subcutaneously, intradermally, intramuscularly, transdermally, intranasally, mucosally, and by aerosol administration. For example, the composition can be administered by inhalation, e.g., as a nasal or mouth spray or aerosol. The compositions may also be delivered in situ, e.g., by implantation.

A pharmaceutically or therapeutically effective amount of the polypeptide of interest will be delivered to the subject. The precise effective amount will vary from subject to subject and will depend upon the species, age, the subject's size and health, the nature and extent of the condition being treated, recommendations of the treating physician, and the therapeutics or combination of therapeutics selected for administration. Thus, the effective amount for a given situation can be determined by routine experimentation. For purposes of the present invention, generally a therapeutic amount will be in the range of about 0.1 µg/kg to about 100 mg/kg, more preferably about 1 µg/kg to about 1 mg/kg, and most preferably about 2 µg/kg to about 100 µg/kg, in at least one dose. The subject may be administered as many doses as is required to reduce and/or alleviate the signs, symptoms, or causes of the disorder in question, or bring about any other desired alteration of a biological system.

The compositions can be used for a variety of purposes, depending on the polypeptide entrapped in the microparticle. For example, for IGF-1, the compositions of the present invention may be used to e.g., stimulate growth of cells in vitro or in vivo in a number of tissues and cell types. The compositions can also be used for bone repair and replacement therapy, to treat osteoporosis or osteoarthritis, to inhibit an inflammatory response, ischemic injury, and organ rejection upon transplantation, to treat pancreatic, liver, kidney, nerve and cardiac disorders, and to increase lactation and meat production in cattle and other farm animals.

Not only can the microparticles be used therapeutically, as described above, the compositions may also be used as vaccines, in order to generate an immune response, or to prepare antibodies, both polyclonal and monoclonal, for, e.g., diagnostic purposes, as well as for immunopurification of the polypeptide of interest. If polyclonal antibodies are desired, a selected mammal, (e.g., mouse, rabbit, goat, horse, etc.) is immunized with the compositions of the present invention. In order to enhance immunogenicity, an immunological adjuvant is generally used with the compositions and the antigen can be linked to a carrier. Immunization for the production of antibodies is generally performed by injecting the composition parenterally (generally subcutaneously or intramuscularly). The animal is usually boosted 2–6 weeks later with one or more injections of the antigen. Polyclonal antisera is then obtained from the immunized animal and treated according to known procedures. See, e.g., Jurgens et al. (1985) *J. Chrom.* 348:363–370.

Monoclonal antibodies are generally prepared using the method of Kohler and Milstein, *Nature* (1975) 256:495–96, or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of non-specifically adherent cells) by applying a cell suspension to a plate or well coated with the protein antigen. B cells, expressing membrane-bound immunoglobulin specific for the antigen, will bind to the plate, and are not rinsed away with the rest of the suspension. Resulting B cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected monoclonal antibody-secreting hybridomas are then cultured either in vitro (e.g., in tissue culture bottles or hollow fiber reactors), or in vivo (as ascites in mice). See, e.g., M. Schreier et al., *Hybridoma Techniques* (1980); Hammerling et al., *Monoclonal Antibodies and T-cell Hybridomas* (1981); Kennett et al., *Monoclonal Antibodies* (1980); see also U.S. Pat. Nos. 4,341,761; 4,399,121; 4,427,783; 4,444,887; 4,452,570; 4,466,917; 4,472,500, 4,491,632; and 4,493,890. Panels of monoclonal antibodies produced against the polypeptide of interest can be screened for various properties; i.e., for isotype, epitope, affinity, etc.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Preparation of rhIGF-1-PLG Microparticles (20% w/w)

Recombinant human IGF-1 (rhIGF-1) for use in these experiments was recombinantly produced in the yeast strain *Pichia pastoris* and purified essentially as described in U.S. Pat. Nos. 5,324,639, 5,324,660, 5,650,496 and International Publication No. WO 96/40776. Following isolation, IGF-1 was formulated into microparticles. Materials used to formulate the microparticles were as follows:

(1) 400 mg of the polymer poly(D,L-lactide-co-glycolide) composed of a 50:50 mol ratio of lactide to glycolide with a molecular weight average of 22 Kdal, (Boehringer Ingelheim Resomer RG 502H), was dissolved in 2.5 ml of methylene chloride (DCM, HPLC grade, obtained from Aldrich Chemicals, U.S.A.) to render a 16% PLG solution;

(2) 10% polyvinyl alcohol (PVA) 23,000 MW (Aldrich Chemicals, U.S.A.) in water; and (3) rhIGF-1, in 0.1 M acetic acid, pH 4.5 (112 mg/ml).

Three separate batches of rhIGF-1 PLG microparticles at a theoretical loading of 20% w/w, were prepared using the following process. Prior to entrapment in the PLG microparticle, the protein was first prepared in a highly concentrated, viscous form by adjusting the pH of a rhIGF-1 buffered solution. This method is described in detail in commonly owned, copending U.S. patent application Ser. No. 60/096,081, entitled "Novel IGF-1 Composition and Its Use," filed Aug. 11, 1998 and incorporated herein by reference in its entirety.

Briefly, preparation by pH adjustment of a rhIGF-1 buffered solution was achieved as follows. 0.5 ml of an rhIGF-1 solution (112 mg/ml) at pH 4.5 was taken and the solubility of the rhIGF-1 was changed by increasing the pH of the solution with 0.1 M sodium hydroxide to 5.5–6.0. This caused the majority of the rhIGF-1 to precipitate as a highly concentrated, opalescent viscous syrup having a concentration of rhIGF-1 of about 350 mg/ml.

Alternatively, the syrup form of rhIGF-1 was prepared by taking bulk rhIGF-1 at a concentration of 13 mg/ml, concentrating it to 74 mg/ml in an initial buffer solution at pH 4.0 and then dialyzing this solution against a 10 mM sodium citrate/140 mM sodium chloride buffer at pH 6.0 using spectra pore tubing 1000 MWCO. The buffer solution was decanted off and the precipitated polypeptide recovered in the form of the viscous syrup.

The rhIGF-1 syrup may also be prepared by removal of a solubility enhancer from a rhIGF-1 solution containing the solubility enhancer as disclosed in commonly owned, copending U.S. patent application Ser. No. 60/096,081, entitled "Novel IGF-1 Composition and Its Use," filed Aug. 11, 1998. In this manner, arginine is used as a solubility enhancer to prepare a high concentration IGF-1 solution from which the solubilizing agent is removed to precipitate the IGF-1 syrup form of the present invention. For example, rhIGF-1 at 100 mg/ml in 10 mM sodium citrate, 120 mM arginine, pH 6.0 is dialyzed against 10 mM sodium citrate, 140 mM sodium chloride, pH 6.0 at 4° C. Under these conditions, rhIGF-1 is only soluble to about 10 mg/ml. Of the original 100 mg/ml, 90 mg/ml precipitates to form the highly concentrated syrup and 10 mg/ml remains in solution. The soluble portion of the rhIGF-1 syrup can be decanted off and the rhIGF-1 syrup recovered.

The density of the IGF-I syrup was determined by weight at ambient temperature (23° C.). 10 ml of IGF-I syrup was prepared volumetrically and its weight determined on a Mettler AE240. the weight of the 10 ml sample of IGF-I syrup was determined to be 10.7 grams. Therefore, the density of the IGF-I syrup was determined to be 1.07 g/ml.

The viscosity of the IGF-I syrup was determined with a Cannon Instruments LV2000 Rotary Viscometer. The instrument was calibrated with a viscosity standard provided by the manufacturer. All measurements were performed at ambient temperature. The viscosity of the IGF-I syrup was determined to be approximately 15,700 centipoise.

The recovered rhIGF-1 syrup was then encapsulated in PLG microparticles as follows. The rhIGF-1 syrup was cooled to 4° C. and 1.4 ml of the PLG solution was added. The mixture was homogenized at 10,000 rpm on an ultra turrex homogenizer for 2.5 minutes at 4° C. This resulted in the formation of a viscous w/o emulsion. This emulsion was poured into 20 ml of the 10% PVA and stirred at 500 rpm on a magnetic stirrer overnight to allow the methylene chloride to evaporate.

The multiple emulsion was then centrifuged at 30,000 G and the pellet which was composed of rhIGF-1-PLG microparticles, recovered and washed twice with distilled water to eliminate free PVA on the surface of the microparticles. The microparticles were freeze-dried and stored in a desiccator.

EXAMPLE 2

In Vitro Release Profile of rhIGF-1-PLG Microparticles (20% w/w)

The three batches of rhIGF-1 prepared as described in Example 1, were used in an in vitro release study at 37° C. Several 3 ml vials, each containing 10 mg of microparticles, were weighed, 1 ml PBS was added to each vial and the vials were kept at 37° C. At each time point indicated, 1 vial was withdrawn and the supernatant assayed for protein concentration using blank microparticles as control. IGF-1 concentration was estimated using a standard BCA assay (Sigma Chemicals, St. Louis, Mo.). The cumulative release was plotted versus time (see FIG. 1). As is readily seen, sustained, steady release of IGF-1 was achieved for at least three weeks.

EXAMPLE 3

Analysis of In Vitro-Released rhIGF-1

Four time points from the above in vitro study, day 1, 7, 14 and 21, were selected to analyze the quality of the rhIGF-1 released from the PLG microparticles. The analysis was carried by three techniques, CN-RP-HPLC, SDS PAGE and a mitogenic bioassay. The mitogenic bioassay was conducted by determining the effect of IGF-1 on proliferating human osteosarcoma MG-63 cells, followed by MTT staining. See, e.g., Lopaczynski et al., *Regulatory Peptides* (1993) 48:207–216. Absorbance was read at 570 nm. Optical density (O.D.) was corrected using activity of a standard IGF-1 in International Units (I.U.). The results are summarized in Tables 1–3.

TABLE 1

In Vitro Release of rhIGF-1 from
Three PLG/rhIGF-1 Batches CN-RP-HPLC Analysis*

| Sample | % Purity | % Main Peak |
|---|---|---|
| Std/MICPLOO2 | 98.52 | 92.56 |
| Batch I/Day 1 | 96.18 | 89.45 |
| Batch I/Day 7 | 96.10 | 89.31 |
| Batch I/Day 14 | 95.62 | 88.83 |
| Batch I/Day 21 | 95.78 | 89.35 |
| Batch II/Day 1 | 95.70 | 88.95 |
| Batch II/Day 7 | 95.67 | 88.92 |
| Batch II/Day 14 | 95.73 | 88.97 |
| Batch II/Day 21 | 95.74 | 89.29 |
| Batch III/Day 1 | 95.74 | 88.96 |
| Batch III/Day 7 | 95.75 | 88.93 |
| Batch III/Day 14 | 95.62 | 88.81 |
| Batch III/Day 21 | 95.84 | 89.37 |

*Peaks area are expressed as a % of the total peak for each sample.

TABLE 2

In Vitro Release of rhIGF-1 from Three
PLG/rhIGF-1 Batches Non-reducing
SDS-PAGE Analysis (Colloidal Coomassie)*

| Sample | % Monomer | % Dimer | % Others |
|---|---|---|---|
| Std/MICPLOO2 | 100 | 0 | 0 |
| Batch I/Day 1 | 100 | 0 | 0 |
| Batch I/Day 7 | 100 | 0 | 0 |
| Batch I/Day 14 | 100 | 0 | 0 |
| Batch I/Day 21 | 100 | 0 | 0 |
| Batch II/Day 1 | 100 | 0 | 0 |
| Batch II/Day 7 | 100 | 0 | 0 |
| Batch II/Day 14 | 100 | 0 | 0 |
| Batch II/Day 21 | 100 | 0 | 0 |
| Batch III/Day 1 | 100 | 0 | 0 |
| Batch III/Day 7 | 100 | 0 | 0 |
| Batch III/Day 14 | 100 | 0 | 0 |
| Batch III/Day 21 | 100 | 0 | 0 |

*Each gel was scanned and gel bands converted to peak intensities. Bands are expressed as a % of the total peak area for each sample. "Other" indicates any peak larger than monomer (dimer, trimer, etc.)

TABLE 3

In Vitro Release of rhIGF-1 from Three
PLG/rhIGF-1 Batches Mitogenic Bioassay*

| Sample | IU/mg$^2$ | % Activity |
|---|---|---|
| Std/MICPLOO2 | 1220 | 93.8 |
| Batch I/Day 1 | 1260 | 96.9 |
| Batch I/Day 7 | 1400 | 107.6 |
| Batch I/Day 14 | 1280 | 98.4 |
| Batch I/Day 21 | 1380 | 106.1 |
| Batch II/Day 1 | 1320 | 101.53 |
| Batch II/Day 7 | 1090 | 83.8 |
| Batch II/Day 14 | 1460 | 112.3 |
| Batch II/Day 21 | 1360 | 104.6 |
| Batch III/Day 1 | 1320 | 101.5 |
| Batch III/Day 7 | 1410 | 108.4 |
| Batch III/Day 14 | 1260 | 96.9 |
| Batch III/Day 21 | 1880 | 144.6 |

*1 mg rhIGF-1 = 1300 IU

As can be seen in Tables 1–3, most of the protein retained the native structure and the IGF-1 remained stable and active over the three weeks. It is especially notable that the protein remained stable in the absence of stabilizing excipients.

EXAMPLE 4

Preparation of rhIGF-1-PLG Microparticles (4% w/w)

Three separate batches of rhIGF-1 PLG microparticles at a theoretical loading of 4% w/w were prepared using the following process. 0.5 ml of the rhIGF-1 solution described in Example 1 was treated, also as described in Example 1, to render the rhIGF-1 in the form of a highly concentrated, viscous syrup. The rhIGF-1 syrup was cooled to 4° C. and 8.75 ml of the 16% PLG solution in methylene chloride, described in Example 1, was added. The mixture was homogenized as described above. The emulsion was added to 40 ml of 10% PVA and stirred at 500 rpm on a magnetic stirrer overnight to allow the methylene chloride to evaporate.

The multiple emulsion was then centrifuged at 30,000 G and the pellet which was composed of rhIGF-1-PLG microparticles, was recovered and washed twice with distilled water to eliminate free PVA on the surface of the microparticles. The microparticles were freeze-dried and stored in a desiccator.

EXAMPLE 5

In Vitro Release Profile of rhIGF-1-PLG Microparticles (4% w/w)

Figure 2:
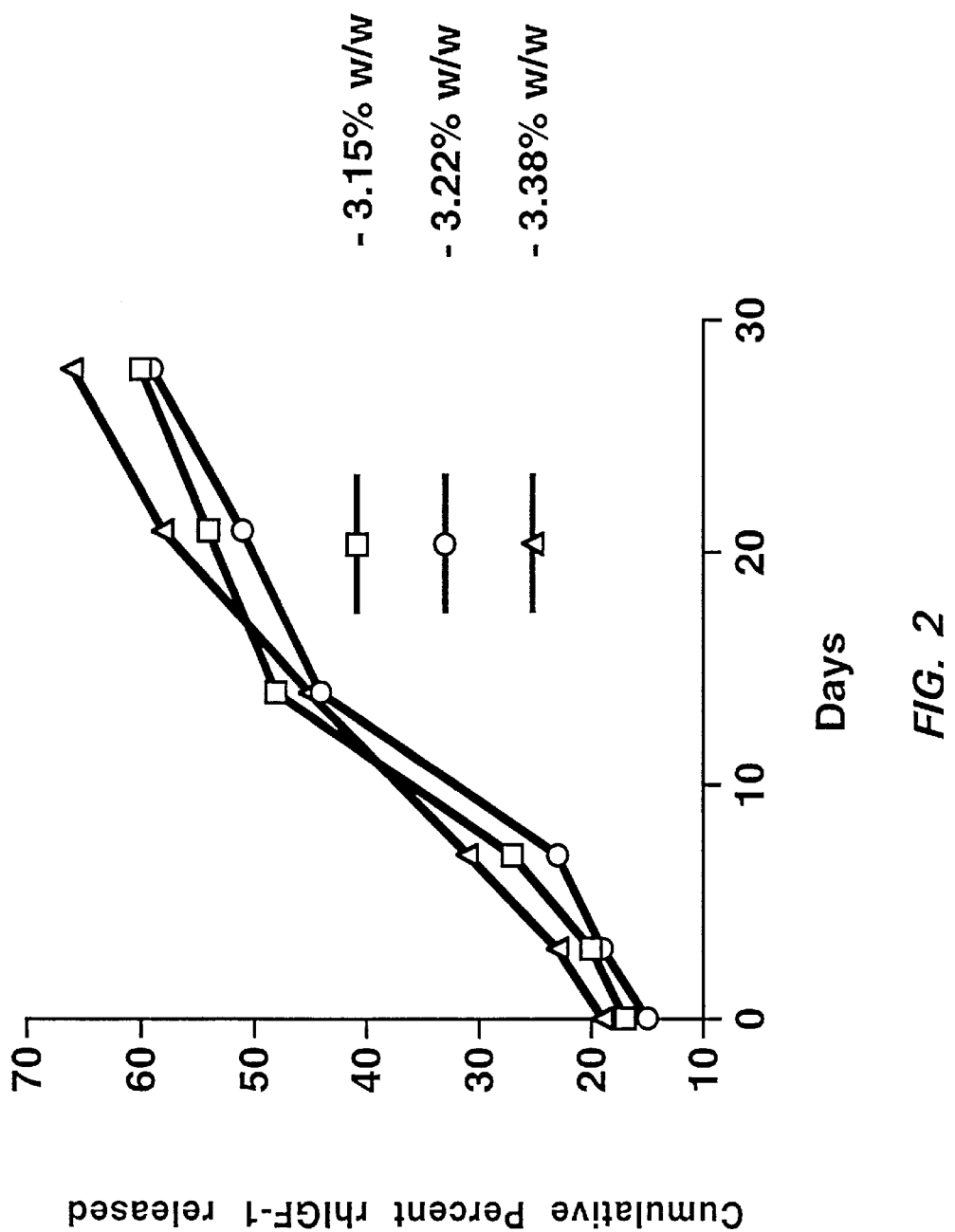
FIG. 2 is a graphical release profile of IGF-1 from PLG microparticles containing an IGF-1 load of 3.15% (squares), 3.22% (circles) and 3.38% (triangles).

The three batches of rhIGF-1 prepared as described in Example 1, were used in an in vitro release study at 37° C., as described in Example 2. Release was plotted versus time (see FIG. 2). As is readily seen, sustained, steady release of IGF-1 was achieved for at least four weeks.

EXAMPLE 6

In Vivo Release Studies of rhIGF-1-PLG Microparticles (17.7% w/w)

Figure 3:
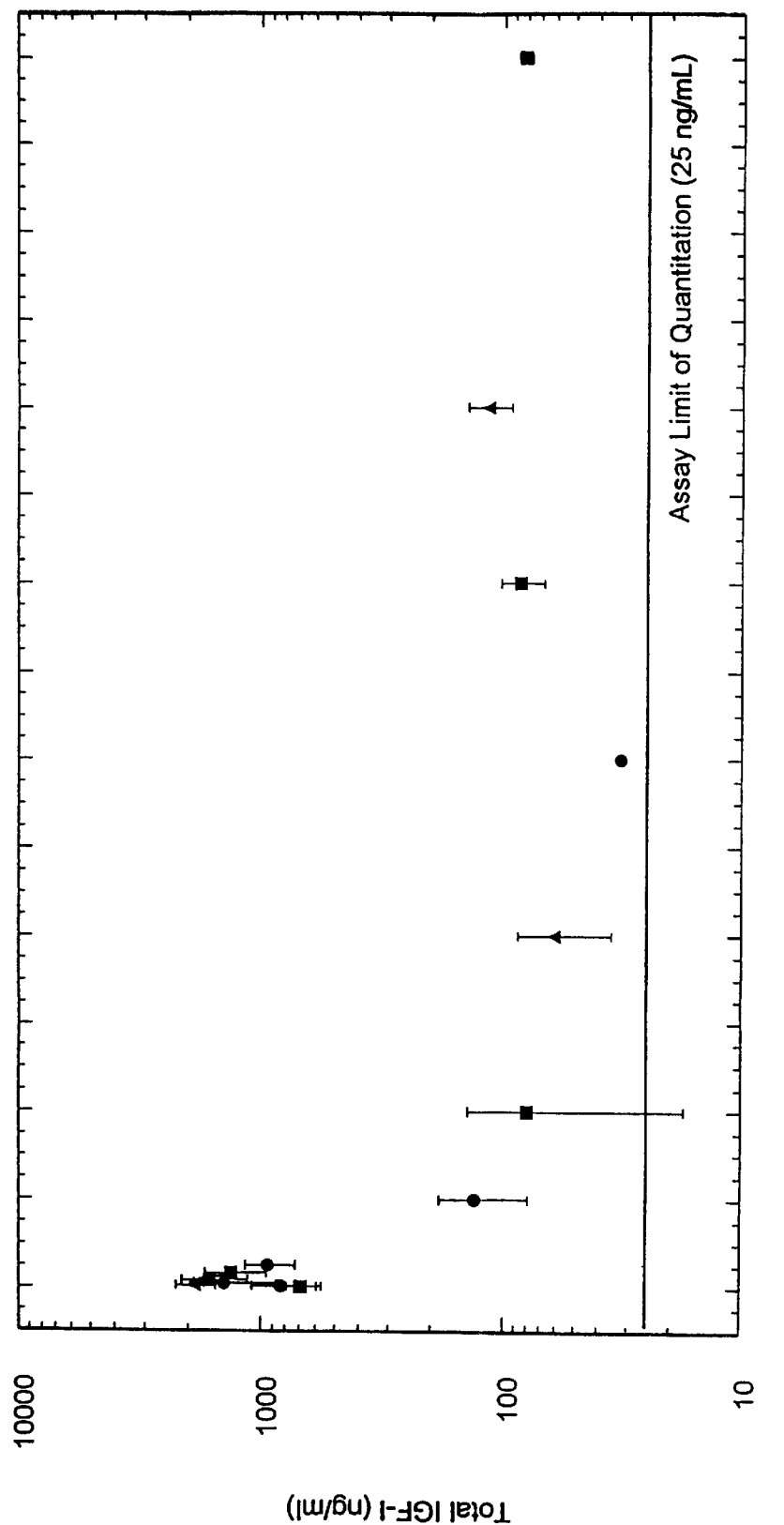
FIG. 3 shows the serum concentrations of IGF-1 over time from in vivo release studies in animals administered microparticles containing 17.7% w/w IGF-1.
Figure 4:
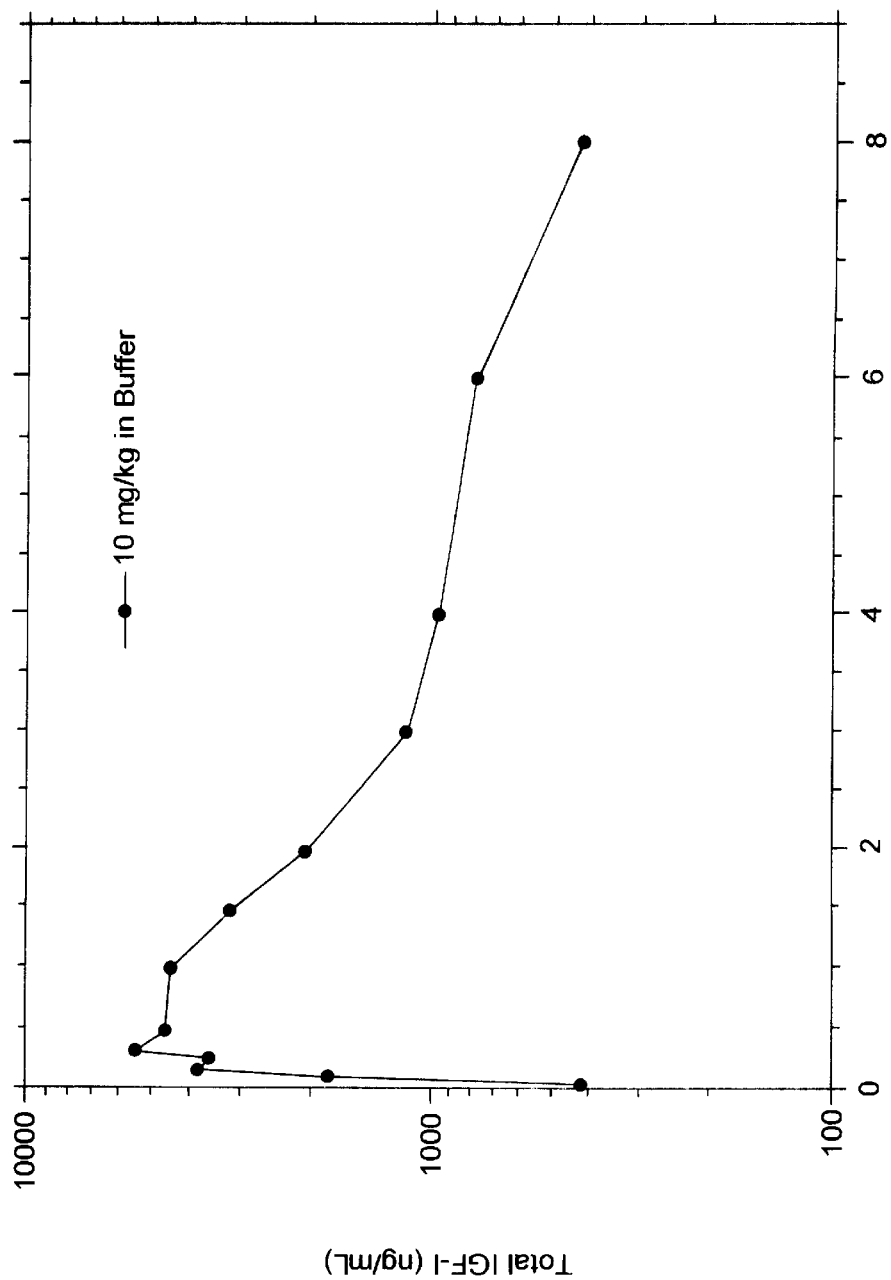
FIG. 4 shows the serum concentrations of IGF-1 over time from control animals administered IGF-1 without microparticles.

40 mg/kg of the microparticles containing 17.7% w/w IGF-1, prepared as described in Example 1, were administered subcutaneously to male CD rats. 9 rats were evaluated, 3 rats per sampling point at the times indicated in FIGS. 3 and 4. 0.5 ml blood was collected from the jugular vein prior to dosing and at each sampling point. Control rats were administered 10 mg/kg IGF-1 in buffer without microparticles. Blood samples were assayed for serum concentrations of IGF-1 using a standard IGF-1 ELISA.

As can be seen in FIG. 3, the microparticles provided continuous release of IGF-1 for at least 336 hours (2 weeks). As shown in FIG. 4, serum concentrations of IGF-1 in rats given the control formulations dropped to initial levels by 8 hours post-administration. Therefore, microparticles prepared using the techniques of the present invention provide for the controlled release of IGF-1 for prolonged periods of time.

EXAMPLE 7

In Vivo Release Studies of rhIGF-1-PLG Microparticles (3.17% w/w)

25 mg/kg of the microparticles containing 3.17% w/w IGF-1, prepared as described in Example 4, were administered subcutaneously to male CD rats. 9 rats were evaluated, 3 rats per sampling point at the times indicated in Table 4. Blood samples were collected for 34 days for the analysis of IGF-1 and glucose. Serum IGF-1 concentration was measured by ELISA assay.

Figure 5:
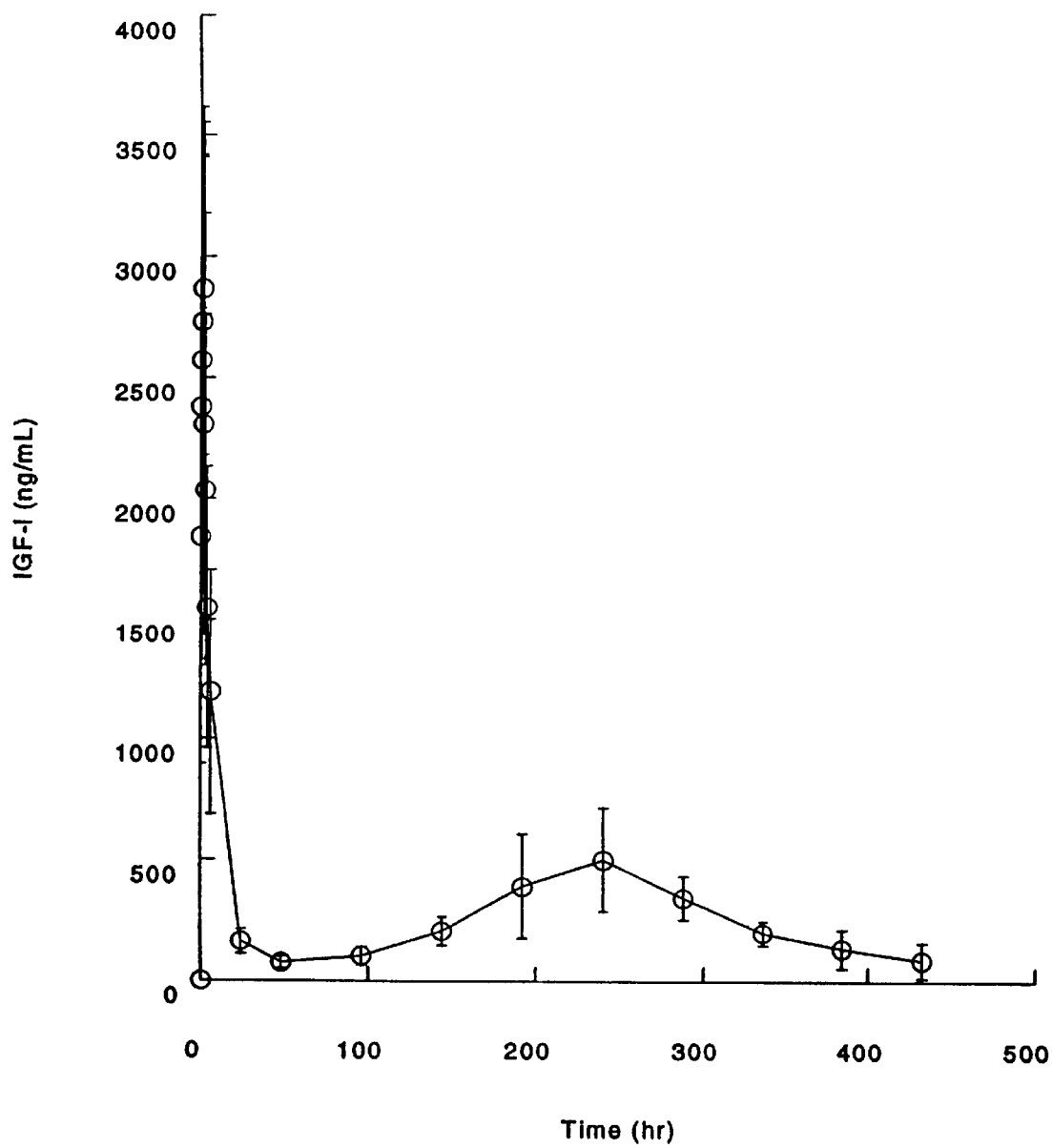
FIG. 5 shows the serum concentrations of IGF-1 over time from in vivo release studies in animals administered microparticles containing 3.17% w/w IGF-1.
Figure 6:
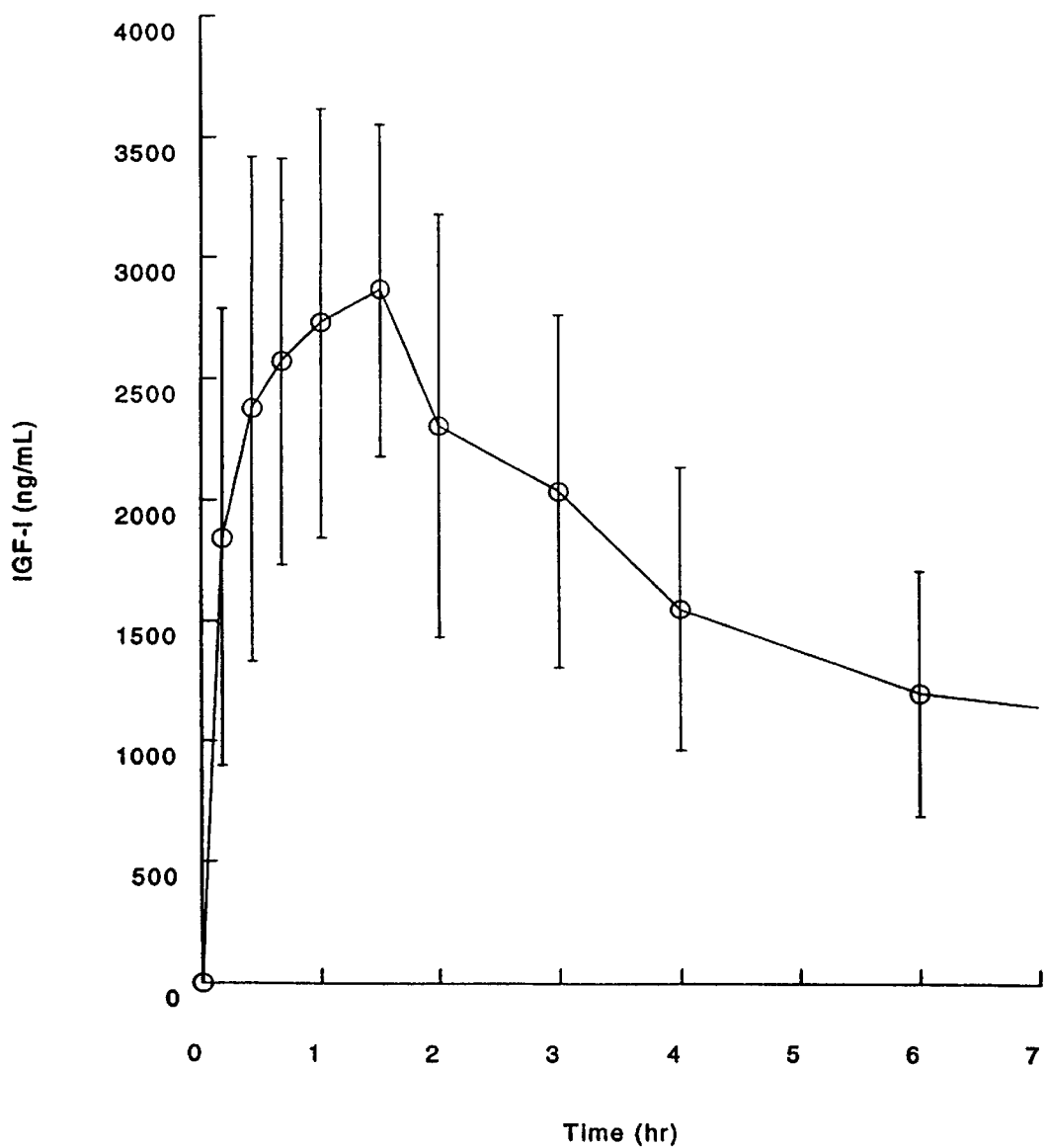
FIG. 6 shows the serum concentrations of IGF-1 for the first six hours from in vivo release studies in animals administered microparticles containing 3.17% w/w IGF-1.

A significant burst was observed during the first 6 hours after administration with a mean (±SD) Cmax of 2868±686 ng/ml at 1.5 hours from the 9 rats (Table 4 and FIGS. 5 and 6). IGF-1 concentrations declined to 77±24 ng/ml at 48 hours and slowly increased to 504±214 ng/ml at 10 days after dosing. No IGF-1 concentrations were detectable (<25 ng/ml) after 18 days. These results indicated that the IGF-1 low-load PLG formulation was associated with an initial burst followed by a sustained release phase which lasted for approximately 18 days in rats. The results were similar to those of the IGF-1 high-load PLG formulation. However, the burst was greater in this study. Also, the low-load formulation produced higher IGF-1 concentrations in the rats despite a smaller dose (25 mg/kg compared to 40 mg/kg in the high-load formulation study).

The initial burst of IGF-1 concentrations caused significant hypoglycemia in all rats which required IP glucose treatment. However, all rats recovered by six hours. Nodules at the injection sites were observed in a few rats during the first week. These nodules disappeared in week 2.

TABLE 4

Mean IGF-1 Concentration versus Time Data (n = 9)

| Time (Hr) | Mean | sd | % cv |
|---|---|---|---|
| 0 | 0 | 0 | 0 |
| 0.167 | 1843 | 944 | 51 |
| 0.417 | 2377 | 1044 | 44 |
| 0.667 | 2573 | 840 | 33 |
| 1 | 2732 | 887 | 32 |
| 1.5 | 2868 | 686 | 24 |
| 2 | 2307 | 871 | 38 |
| 3 | 2035 | 728 | 36 |
| 4 | 1549 | 585 | 38 |
| 6 | 1198 | 508 | 42 |
| 24 | 164 | 53 | 32 |
| 48 | 77 | 24 | 31 |
| 96 | 105 | 40 | 38 |
| 144 | 209 | 60 | 29 |
| 192 | 394 | 215 | 55 |
| 240 | 504 | 214 | 42 |
| 288 | 346 | 89 | 26 |
| 336 | 202 | 50 | 25 |
| 384 | 136 | 81 | 60 |
| 432 | 89 | 74 | 83 |

Thus, novel microparticles and methods of making and using the same are disclosed. Although preferred embodiments of the subject invention have been described in some detail, it is understood that obvious variations can be made without departing from the spirit and the scope of the invention as defined by the appended claims.

We claim:

1. A method of making a microparticle comprising:
   (a) providing a low salt-containing aqueous polypeptide composition at a pH about 5.5 or greater comprising biologically active human insulin-like growth factor-1 (IGF-1) or biologically active analog thereof, wherein said IGF-1 analog has at least 80% amino acid sequence identity to the amino acid sequence of human IGF-1, and wherein said human IGF-1 or analog thereof is present in a concentration of 250 mg/ml to 500 mg/ml;
   (b) adding said low salt-containing polypeptide composition to a solution of a polymer comprising a poly(α-hydroxy acid), wherein said polymer is present at a concentration of about 1%–30% in an organic solvent and further wherein said IGF-1 or analog thereof is present at 0.1% to about 40% (w/w) in the polymer/polypeptide solution;
   (c) emusifying the polymer/polypeptide solution to form an emulsion;
   (d) adding an emulsion stabilizer to the emulsion to form microparticles;
   (e) removing organic solvent from the stabilized emulsion; and
   (f) recovering the microparticles.

2. The method of claim 1, wherein said low salt-containing polypeptide composition is cooled to a temperature of about 2° C. to about 8° C. prior to step (b).

3. The method of claim 2, wherein said low salt-containing polypeptide composition is cooled to a temperature of about 4° C.

4. The method of claim 1, wherein the polymer is a poly(α-hydroxy acid) selected from the group consisting of poly(L-lactide), poly(D,L-lactide) and poly(D,L-lactide-co-glycolide).

5. The method of claim 4, wherein the polymer is poly(D,L-lactide-co-glycolide).

6. The method of claim 1, wherein the IGF-1 or IGF-1 analog present in step (b) is present at about 3% to about 20% (w/w).

7. The method of claim 1, wherein the IGF-1 or IGF-1 analog present in step (b) is present at about 3% to about 4% (w/w).

8. The method of claim 1, wherein the IGF-1 or IGF-1 analog present in step (b) is present at about 18% to about 20% (w/w).

9. A method of making a microparticle comprising:
   (a) preparing a low salt-containing aqueous polypeptide composition at a pH about 5.5 or greater comprising biologically active human insulin-like growth factor-1 (IGF-1) or biologically active analog thereof, wherein said IGF-1 analog has at least 95% amino acid sequence identity to the amino acid sequence of human IGF-1, and wherein said human IGF-1 or analog thereof is present in a concentration of 250 mg/ml to 500 mg/ml;
   (b) cooling said low salt-containing polypeptide composition to a temperature of about 2° C. to about 8° C.;
   (c) adding said cooled polypeptide composition to a solution of a poly(α-hydroxy acid) polymer selected from the group consisting of poly(L-lactide), poly(D, L-lactide) and poly(D,L-lactide-co-glycolide), wherein said polymer is present at a concentration of about 5%–20% in methylene chloride and further wherein said IGF-1 or analog thereof is present at about 3% to about 20% (w/w) in the polymer/polypeptide solution;
   (d) emusifying the polymer/polypeptide solution to form an emulsion;
   (e) adding polyvinyl alcohol as an emulsion stabilizer to the emulsion to form microparticles;
   (f) removing methylene chloride from the stabilized emulsion; and
   (g) recovering the microparticles.

10. The method of claim 9, wherein said low salt-containing polypeptide composition is cooled to a temperature of about 4° C.

11. The method of claim 9, wherein the polymer is poly(D,L-lactide-co-glycolide).

12. The method of claim 9, wherein said IGF-1 or said IGF-1 analog present in step (c) is present at about 3% to about 4% (w/w).

13. The method of claim 9, wherein said IGF-1 or said IGF-1 analog present in step (c) is present at about 18% to about 20% (w/w).

14. The method of claim 9 wherein said low salt-containing polypeptide composition in step (a) comprises a solubility enhancer.

15. The method of claim 14 wherein said solubility enhancer is arginine or an arginine analog.

16. The method of any one of claims 9, 14 or 15, wherein said low salt-containing polypeptide composition in step (a) is present at a pH from about 5.5 to about 9.0.

17. A method of making a microparticle comprising:
   (a) preparing a low salt-containing aqueous polypeptide composition at a pH about 5.5 or greater comprising biologically active human insulin-like growth factor-1 (IGF-1) or biologically active analog thereof, wherein said IGF-1 analog has at least 80% amino acid sequence identity to the amino acid sequence of human IGF-1, and wherein said human IGF-1 or analog thereof is present in a concentration of 250 mg/ml to 500 mg/ml;
   (b) cooling said low salt-containing polypeptide composition to a temperature of about 2° C. to about 8° C.;
   (c) adding said cooled polypeptide composition to a solution of a poly(α-hydroxy acid) polymer selected from the group consisting of poly(L-lactide), poly(D, L-lactide) and poly(D,L-lactide-co-glycolide), wherein said polymer is present at a concentration of about 5%–20% in methylene chloride and further wherein said IGF-1 or analog thereof is present at about 3% to about 20% (w/w) in the polymer/polypeptide solution;
   (d) emusifying the polymer/polypeptide solution to form an emulsion;
   (e) adding polyvinyl alcohol as an emulsion stabilizer to the emulsion to form microparticles;
   (f) removing methylene chloride from the stabilized emulsion; and
   (g) recovering the microparticles.

18. The method of claim 17, wherein said low salt-containing polypeptide composition is cooled to a temperature of about 4° C.

19. The method of claim 17, wherein the polymer is poly(D,L-lactide-co-glycolide).

20. The method of claim 17, wherein said IGF-1 or said IGF-1 analog present in step (c) is present at about 3% to about 4% (w/w).

21. The method of claim 17, wherein said IGF-1 or said IGF-1 analog present in step (c) is present at about 18% to about 20% (w/w).

22. The method of claim 17 wherein said IGF-1 or said IGF-1 analog in step (a) comprises a solubility enhancer.

23. The method of claim 17 wherein said solubility enhancer is arginine or an arginine analog.

24. The method of any one of claims 17, 22 or 23, wherein said low salt-containing polypeptide composition in step (a) is present at a pH from about 5.5 to about 9.0.

25. A method of making a microparticle comprising:
   (a) preparing a low salt-containing aqueous polypeptide composition at a pH about 5.5 or greater comprising biologically active human insulin-like growth factor-1 (IGF-1) or biologically active analog thereof, wherein said IGF-1 analog has at least 90% amino acid sequence identity to the amino acid sequence of human IGF-1, and wherein said human IGF-1 or analog thereof is present in a concentration of 250 mg/ml to 500 mg/ml;
   (b) cooling said low salt-containing polypeptide composition to a temperature of about 2° C. to about 8° C.;
   (c) adding said cooled polypeptide composition to a solution of a poly(α-hydroxy acid) polymer selected from the group consisting of poly(L-lactide), poly(D, L-lactide) and poly(D,L-lactide-co-glycolide), wherein said polymer is present at a concentration of about 5%–20% in methylene chloride and further wherein said IGF-1 or analog thereof is present at about 3% to about 20% (w/w) in the polymer/polypeptide solution;
   (d) emusifying the polymer/polypeptide solution to form an emulsion;
   (e) adding polyvinyl alcohol as an emulsion stabilizer to the emulsion to form microparticles;
   (f) removing methylene chloride from the stabilized emulsion; and
   (g) recovering the microparticles.

26. The method of claim 25, wherein said low salt-containing polypeptide composition is cooled to a temperature of about 40° C.

27. The method of claim 25, wherein the polymer is poly(D,L-lactide-co-glycolide).

28. The method of claim 25, wherein said IGF-1 or said IGF-1 analog present in step (c) is present at about 3% to about 4% (w/w).

29. The method of claim 25, wherein said IGF-1 or said IGF-1 analog present in step (c) is present at about 18% to about 20% (w/w).

30. The method of claim 25 wherein said low salt-containing polypeptide composition in step (a) comprises a solubility enhancer.

31. The method of claim 30 wherein said solubility enhancer is arginine or an arginine analog.

32. The method of any one of claims 25, 30 or 31, wherein said low salt-containing polypeptide composition in step (a) is present at a pH from about 5.5 to about 9.0.

33. A method of making a microparticle comprising:
  (a) preparing a low salt-containing aqueous polypeptide composition at a pH about 5.5 or greater comprising biologically active human insulin-like growth factor-1 (IGF-1) wherein said human IGF-1 is present in a concentration of 250 mg/ml to 500 mg/ml;
  (b) cooling said low salt-containing polypeptide composition to a temperature of about 2° C. to about 8° C.;
  (c) adding said cooled polypeptide composition to a solution of a poly(α-hydroxy acid) polymer selected from the group consisting of poly(L-lactide), poly(D,L-lactide) and poly(D,L-lactide-co-glycolide), wherein said polymer is present at a concentration of about 5%–20% in methylene chloride and further wherein said IGF-1 is present at about 3% to about 20% (w/w) in the polymer/IGF-1 solution;
  (d) emusifying the polymer/IGF-1 solution to form an emulsion;
  (e) adding polyvinyl alcohol as an emulsion stabilizer to the emulsion under conditions that allow microparticles to form;
  (f) removing organic solvent from the stabilized emulsion; and
  (g) recovering the microparticles.

34. A method of making a microparticle comprising:
  (a) preparing a low salt-containing aqueous polypeptide composition at a pH about 5.5 or greater comprising biologically active human insulin-like growth factor-1 (IGF-1) wherein said human IGF-1 is present in a concentration of 250 mg/ml to 500 mg/ml;
  (b) cooling said low salt-containing polypeptide composition to a temperature of about 4° C.;
  (c) adding said cooled polypeptide composition to a solution of a poly(D,L-lactide-co-glycolide) polymer, wherein said polymer is present at a concentration of about 5%–20% in methylene chloride and further wherein said IGF-1 is present at about 3% to about 20% (w/w) in the polymer/IGF-1 solution;
  (d) emusifying the polymer/IGF-1 solution to form an emulsion;
  (e) adding polyvinyl alcohol as an emulsion stabilizer to the emulsion under conditions that allow microparticles to form;
  (f) removing organic solvent from the stabilized emulsion; and
  (g) recovering the microparticles.

35. The method of any one of claims 33 or 34, wherein said IGF-1 present in step (c) is present at about 3% to about 4% (w/w).

36. The method of any one of claims 33 or 34, wherein said IGF-1 present in step (c) is present at about 18% to about 20% (w/w).

37. The method of any one of claims 33 or 34, wherein said low salt-containing polypeptide composition in step (a) is present at a pH from about 5.5 to about 9.0.

38. The method of any one of claims 33 or 34 wherein said low salt-containing polypeptide composition in step (a) comprises arginine or an arginine analog.

39. The method of claim 38, wherein said low salt-containing polypeptide composition in step (a) is present at a pH from about 5.5 to about 9.0.

* * * * *